US005348533A

United States Patent [19]

Papillon et al.

[11] Patent Number: 5,348,533

[45] Date of Patent: Sep. 20, 1994

[54] PHERESIS APPARATUS

[75] Inventors: Jean Papillon, St. Germaine-en-laye, France; Frederick J. York, Arlington, Mass.

[73] Assignee: Haemoentics Corporation, Braintree, Mass.

[21] Appl. No.: 936,569

[22] Filed: Aug. 27, 1992

[51] Int. Cl.[5] .................................... A61M 1/00

[52] U.S. Cl. .................................... 604/4; 604/6; 604/19

[58] Field of Search .................... 604/4, 5, 6, 19, 27, 604/48; 494/1, 10, 11, 16, 43

[56] References Cited

U.S. PATENT DOCUMENTS

| | | | |
|---|---|---|---|
| 3,655,123 | 4/1972 | Judson et al. | 233/21 |
| 3,892,236 | 7/1975 | Djerassi | 604/6 |
| 4,086,924 | 5/1978 | Latham, Jr. | 604/6 |
| 4,096,859 | 6/1978 | Agarwal et al. | 128/213 |
| 4,185,629 | 1/1980 | Cullis et al. | 604/6 |
| 4,240,408 | 12/1980 | Schael et al. | 128/1 R |
| 4,416,654 | 11/1983 | Schoendorfer et al. | 494/10 |
| 4,464,167 | 7/1984 | Schoendorfer et al. | 604/6 |
| 4,643,718 | 2/1987 | Marten | 604/28 |
| 4,668,214 | 5/1987 | Reeder | 494/37 |
| 4,954,128 | 9/1990 | Ford | 604/5 |
| 5,045,057 | 9/1991 | Van Driessche et al. | 604/50 |
| 5,211,849 | 5/1993 | Kitaevich et al. | 604/6 X |

FOREIGN PATENT DOCUMENTS

| | | | |
|---|---|---|---|
| 0171749 | 2/1986 | European Pat. Off. . | |
| WO86/00231 | 1/1986 | PCT Int'l Appl. . | |
| WO87/06472 | 11/1987 | PCT Int'l Appl. . | |
| 8806460 | 9/1988 | World Int. Prop. O. | 604/6 |

*Primary Examiner*—Robert A. Hafer
*Assistant Examiner*—Sam Rimell
*Attorney, Agent, or Firm*—Hamilton, Brook, Smith & Reynolds

[57] ABSTRACT

The length of time required to draw, centrifugally separate, harvest blood components and return blood components is reduced by providing a two-arm pheresis system in which blood is drawn from one arm, anticoagulated and pumped into an input reservoir then transferred into a centrifuge bowl for separation, while separated blood components are harvested and returned to the donor from an output reservoir via another arm.

30 Claims, 1 Drawing Sheet

PHERESIS APPARATUS

DESCRIPTION

Field of the Invention

This invention relates to the field of blood processing and, more specifically, to pheresis apparatus and procedures for separating whole blood into its constituent components.

Background of the Invention

Whole human blood includes at least three types of specialized cells. These are red blood cells, white blood cells, and platelets. All of these cells are suspended in plasma, a complex aqueous solution of proteins and other chemicals.

Until relatively recently, blood transfusions have been given using whole blood. There is, however, growing acceptance within the medical profession for transfusing only those blood components required by a particular patient instead of using a transfusion of whole blood. Transfusing only those blood components necessary preserves the available supply of blood, and in many cases, is better for the patient. Before blood component transfusions can be widely employed, however, satisfactory blood separation techniques and apparatus must evolve.

Plasmapheresis is the process of taking whole blood from a donor and separating the whole blood into a plasma component and a non-plasma component under conditions whereby the plasma component is retained and the non-plasma component is returned to the donor.

Thrombocytapheresis is similar, except that whole blood is separated into a platelet component and non-platelet component and the platelet component retained or "harvested" and the non-platelet component returned to the donor.

A particularly useful device for the collection of blood cell components is the Haemonetics® 30 Cell Separator Blood Processor manufactured by Haemonetics Corporation, Braintree, Mass. (hereinafter the Model 30). The Model 30 is illustrated in FIG. 1 of U.S. Pat. No. 4,464,167 (as modified by a surge protocol shown in dotted lines). The Model 30 utilizes a conically-shaped centrifuge similar to that described in U.S. Pat. No. 3,145,713, FIG. 6, now called the Latham Bowl. The bowl of the centrifuge is held in a chuck which is attached to a spindle and driven by a motor. The centrifuge consists of a rotor or bowl portion wherein blood component is separated and a stator portion consisting of an input and output port. A rotary seal provides fluid coupling between the stator and the bowl. One side of the input port is connected through blood compatible tubing which is engaged by a first peristaltic pump to a source of whole blood. In a draw cycle, the whole blood is extracted from a donor via a venipuncture made by a phlebotomy needle. Anticoagulant is mixed with the whole blood prior to entry into the centrifuge bowl. The other side of the input port is in fluid communication with a fractionation volume in the rotor.

A return phlebotomy needle is coupled to a reinfusion bag, which in turn is coupled through a second pump and clamp/switches to the output port of the stator portion of the centrifuge.

The rotor is rotated at a fixed speed and various blood fractions are collected at the output port and directed into appropriate containers by diverting the flow through tubing in accordance with the setting of three-way clamp/switches.

Fractionation within the centrifuge is determined by the relative densities of the different cell components being separated and collected. The various cell fractions pass through the outlet port of the centrifuge bowl by progressive displacement from the lower portion of the bowl. An operator is trained to visually observe and assess the boundaries or demarcation lines of different component layers as they approach the outlet port of the centrifuge bowl. When the desired fraction has excited the bowl, the centrifuge is stopped. The flow is then reversed and the uncollected cells, such as packed red blood cells (RBC) are returned to the donor from the reinfusion bag via the return phlebotomy needle. The preceding process is usually repeated six to eight times, or cycles, with the same patient, until a sufficient quantity of cell component has been harvested. The total time of collection from a given patient can range from one and one-half to two hours using this technique.

During the 1980's, Haemonetics Inc., by their models of the V50-series, developed a single needle procedure of automated retransfusion with satisfactory control so that a pheresis donor/patient is protected against return infusion of blood with too high a pressure and against inadvertent administration of air. Thus, drawing blood from the donor/patient, as well as retransfusion, could be carried out through one and the same needle connection. Administration of the plasma (or substitution fluid), needed during any lengthy treatment, is also carried out by allowing the intended volume of such fluid to pass or be drawn by suction through and into the top of the centrifuge bowl, previously rotating, but now standing still, while the bowl is being emptied from the bottom. In this design, the return flow speed is limited, partly because of the high viscosity of the first fraction of retransfused component, which consists of packed red cells. The packed red cells cause increased friction of flow and, consequently, increased internal pressure in the tubing and the receiving blood vessel. The return flow speed is also limited by the capacity of donors/patients to metabolize the anticoagulant, i.e., calcium ion-binding citrate (admixed inter alia as an inhibitor to coagulation), present in the plasma given back to the donor/patient. The V-50 series process therefore takes a relatively long time for retransfusion.

A PCT application, SE/87/00213, based on Swedish Application SE/86/01891-8, filed Apr. 24, 1986 discloses an improvement on the V-50 series single arm procedure which enables more rapid reinfusion to a donor. In the Swedish system, red cells are reinfused at a rapid rate after dilution by mixing with some of the collected plasma.

Another improvement in pheresis procedures involves an elutriation process. By adding an auxiliary pump to the Model 30, the component yield of the process can be enhanced by a so-called "surge protocol". In this protocol, plasma separated in the bowl is pumped by the auxiliary pump back to the bowl through the inlet port and through the red cells suspended in the bowl. Under the influence of the centrifugal force field, and by the process of elutriation, the returned plasma separates the heavier cells (red cells and white cells) from the lighter cells (platelets), all as described in the referenced U.S. Pat. No. 4,464,167. The surge protocol achieves a high degree of components separation by using both centrifugal and elutriation cell separation.

While the above described systems are suitable for the purpose intended, it would be advantageous, particularly in therapeutic procedures if the length of time in which the donor must be connected to the system and the volume of extracorporeal blood (ECV) utilized in the process could be reduced. Both of these factors have an adverse physiological affect on the donor.

SUMMARY OF THE INVENTION

The length of time it takes to draw, separate and return blood taken from a donor is primarily influenced by the rate at which blood can be taken from a given venipuncture site without causing excessive physiological discomfort to the donor. This rate varies from donor to donor and cannot be exceeded. However, what can be done is to utilize the time taken for the draw process to accomplish other things as well. This reduces the dependency of the system on the flow rate through the venipuncture arm.

Thus, in accordance with the present invention, whole blood from a donor is withdrawn at a certain rate via a draw needle, and anticoagulated and stored in an input reservoir, while at the same time, previously withdrawn anticoagulated whole blood stored in the input reservoir is being transferred by a transfer pump at a rate equal to the combined blood and anticoagulant input rates in the centrifuge bowl for separation. Also, while this is occurring, separated cells are being harvested while other components are being stored in an output reservoir from which they are being returned to the donor by a return pump via a return needle. The input and output reservoirs thus act as buffers between the system and the donor and enable the separation process to proceed substantially continuously without regard to the draw and return time limitations. Furthermore, the ECV is minimized in this process by adjusting the pump rates so that once sufficient whole blood is drawn (about 300 ml) to (along with the anticoagulant) fill the centrifuge bowl, the amount of fluid returned is equal to the amount withdrawn, whereby the ECV does not exceed about 300 ml.

The system of the invention for implementing the above method comprises a source of anticoagulant, an input reservoir, a blood component separator, an output reservoir and a plurality of pumps. The pumps are: (a) a draw pump for drawing whole blood form a donor (b) an anticoagulant pump for mixing the whole blood with anticoagulant, (c) a transfer pump for transferring anticoagulated whole blood from the input reservoir to the component separator; and (d) a return pump for returning to the donor a component from the output reservoir. (Note: The separator is preferably of the type having a separation bowl or reservoir in which blood components, such as plasma, platelets and cells are separated into constituent components).

DETAILED DESCRIPTION OF THE INVENTION

Figure 1:
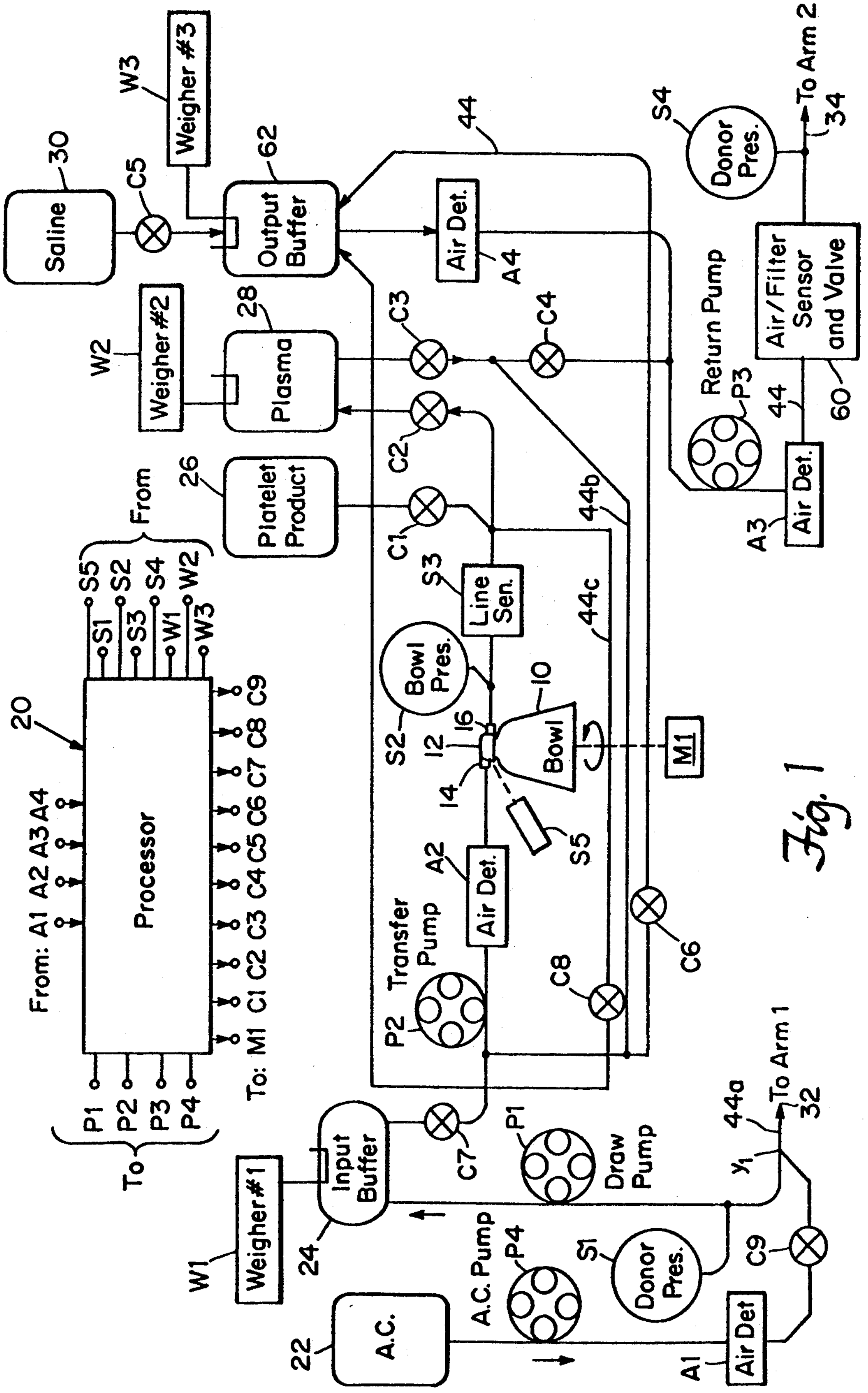
FIG. 1 is a schematic drawing of the apparatus of the invention.

Referring now to FIG. 1, the invention will now be described in detail in connection therewith. Central to the pheresis system of the invention is a blood component separator in the form of a centrifuge shown generally at 40. Preferably, the centrifuge uses a Latham type receptacle or bowl described above in U.S. Pat. No. 3,145,713 in which a volume of blood may be contained while being separated. The centrifuge 40 is comprised of a stationary part 12 and a rotatable part, bowl 10. The stationary part 12 has an inlet port 14 coupled to the interior volume of bowl 10 via rotary seal 18 and an outlet port, also fluidly coupled to the interior volume of bowl 10 via rotary seal 18.

Motor M1 causes the bowl to rotate upon command from processor 20.

Four peristaltic pumps P1, P2, P3 and P4, along with nine solenoid operated clamps C1–C9, control the flow of fluid through the system via biocompatible blood tubing conduits indicated generally by numeral 44. Each pump and clamp is controlled by electrical signals sent from a processor 20.

Air detectors A1–A4 and a detector (not shown) in sensor 60, feed warning signals to the processor 20 in the event air bubbles are detected in any of the conduits 44. Donor blood pressure is also monitored by sensors S1 and S4 coupled to respective phlebotomy needles 32 and 34. The blood pressure information is fed to processor 20. Sensor S2 senses the pressure in the bowl and line sensor S3 detects transitions in the light scattering properties of the fluid passing through the line from bowl 10. These transitions relate to the density and size of the particles suspended in the fluid.

Digital weighers W1, W2 and W3 are attached to respective input reservoir bag 24, plasma bag 18, and output reservoir bag 62 to provide a signal to the processor 20 indicating the volume of fluid collected in the bags. "Draw" phlebotomy needle 32 is connected via a Y-fitment Y1 to anticoagulant bag 22 and input reservoir 24. Whole blood is withdrawn from a donor by making a venipuncture in arm #1 of the donor with draw needle 32 and energizing pumps P1, and P4 and opening clamp C9, in which case, whole blood is mixed with anticoagulant from bag 22 at Y-junction 32 and coupled to input buffer or reservoir 24.

However, before drawing blood from the donor, the system is first operated in a priming mode, then the system is operated in a draw/return mode consisting of a first dynamic cycle, followed by several cycles in a steady state condition and a final cycle before the donor is disconnected from the system. The details of these modes of operation and cycles will now be described.

Priming Mode

In the priming mode, clamps C4, C6, C7 and C8 are closed. The conduit *44a*, leading to needle 32, is manually clamped, and pumps P2 and P3 are deenergized and pumps P4 and P1 are energized. Anticoagulant is transferred using pumps P1 and P4 from bag 22 into input buffer 24, until the weigher W1 indicates to the processor 20 that sufficient anticoagulant is in the lines and no leaks are present.

Next, clamp C5 is opened and saline is dripped by gravity into output buffer bag or reservoir 62. The weight of bag 62 is monitored by weigher W3 to make sure saline is reaching the bag. Return pump P3 is then energized and the phlebotomy line to arm 2 is purged of air using saline from the output buffer 62.

Fill Mode

Assuming the lines have been primed/purged satisfactorily, draw pump P1 and A.C. pump P4 are energized along with motor M1 which rotates bowl 10.

Clamp C2 is opened connecting plasma bag 28 to the bowl output port 16 and C1, C3, C4, C6 and C8 are closed. The manual clamp on the line 44*a* to phlebotomy needle 32 is released and anticoagulated whole blood is drawn by pump P1 into input buffer 24. At the same time, return pump P3 is energized and is slowly pumping saline, or other physiological fluid, from output buffer 62 into the donor arm 2 via return needle 34.

A small amount of anticoagulated whole blood is accumulated in input buffer 24 (20–30 ml) to establish the integrity of the line from the needle 32 to the bag 24, whereupon clamp C7 is opened and transfer pump P2 energized to begin filling centrifuge bowl 10. At this point, the speed of draw pump P2 and transfer pump P3 is adjusted to be about equal, so the weight in input buffer bag 24 (as determined by W1) remains the same, while the bowl is being filled.

Optical sensor S5 sends a signal to the processor 20 when the bowl 10 is full and sensor S3 indicates when plasma is beginning to be displaced out port 16. About 50–100 ml of plasma is allowed to accumulate in plasma bag 28, as determined by weigher W2. At this point, transfer pump P2 is momentarily stopped, clamp C7 is closed, and C3 is opened.

When an optional "surge" protocol is to be conducted, (as described in U.S. Pat. No. 4,464,167) then the surge line 44*b* is primed with plasma. To accomplish this clamps C1, C4, C6 C7 and C8 are closed, and C2 and C3 are opened. Pump P2 then transfers plasma from the plasma bag 28 through line 44*b* toward bowl input port 14. This transfer continues until all air is purged from line 44*b*, which is indicated by air detector A2.

Process Mode

After the surge line is primed the clamps C7 and C8 are opened, while clamps C1, C2, C3, C4 and C6 are closed. Note also that clamp C5 is closed and C9 is open. The draw pump P1 and the A.C. pump P4 are energized so that the input reservoir 24 being filled with anticoagulated whole blood, while at the same time transfer pump P2 is energized to withdraw fluid from buffer 24, at a rate Q2 equal to the inflow rate Q1 into reservoir 24, thereby delivering the contents of the input buffer reservoir 24 through air detector A2 to port 14 of the bowl. This action causes a separated blood component i.e. plasma-A.C. mixture to leave the bowl 10 via port 16, at a rate Q2=Q1, and enter the output buffer 62 via line 44C.

The return pump, P3, is also now energized to remove fluid from the output buffer 60 and direct this flow through air detector A3 and the air/filter sensor 60 for delivery to the donor via the second arm phlebotomy needle 34. The rate of pumping by P3 is made equal to that of Q1 minus Q4, i.e. equal to the blood flow rate taken from the donor. There will be some accumulation of A.C. diluted plasma within the output buffer bag 60 until surge begins, this volume is equal to the amount of A.C. volume pumped during the "plasma generation phase" (Process), this build up is measured by the system using weigher W3.

For a typical procedure Q1=60 ml/min. and Q4=(1/12*Q1)=5 ml/min.; therefore, Q2=60 ml/min. and Q4=55 ml/min. If the donor hematocrit is approximately 0.43 then a complete cycle (product available) requires about 465 ml of whole blood to be drawn. After 250 ml of whole blood and A.C. has been used to fill the bowl (bowl volume) there remains ~235.83 ml to be drawn from the donor.

[465 ml−(250 ml/60 ml/min.)*55 ml/min.]=235.83

At the rates listed above, it takes about 4.167 min. to fill the bowl and 4.288 min. of producing plasma before the platelets are available.

Surge Mode

When Optical Sensor S5 adjacent bowl 10 senses a transition of fluid from plasma to platelets it indicates to the processor 20 that the optional Surge protocol should commence. Transfer pump P2 is then stopped, C2 and C3 are OPENED and C7 and C8 are CLOSED. Next the pump P2 is energized and ramped up in speed to draw out the plasma accumulated in bag 28 during the fill mode. The plasma is drawn out at a constantly increasing rate through clamp C3, and into bowl port 14 then out port 16 returning to bag 28. This serves to improve the separation and quantity of platelets via elutriation. When sensor S3 indicates that platelets are emerging from port 16 clamp C1 is OPENED and C2 is CLOSED, diverting these platelets to bag platelet product 26. The accumulation of platelets continues until S3 has indicated that the platelet density peak has passed. When this has occurred pump P2 is stopped, C1 is CLOSED and C2 OPENED, and the centrifuge motor M1 turned off; the Surge cycle is now completed.

Though the exact time taken for Surge is variable, it is typically found to be around 0.625 minutes. The resulting product volume of platelets is around 35 ml.

The first "Pass", consists of only the above first Fill/-Process/Surge sequence, and takes about 9.28 minutes for the rates given in the example above.

A summary of the fluid transfers for this example is as follows:

The input buffer 24 receives a total inflow of about 544.8 ml; i.e.: 250 ml during Fill, 257.3 ml during Process and 37.5 ml during Surge. The input buffer loses approximately 507.3 ml over this total time period; i.e.: 250 ml during Fill, 257.3 ml during Process and 0 ml during Surge—leaving a net of 37.5 ml in the input buffer 24 as the second pass begins.

The output buffer 62, on the other hand, receives a "trickle" of saline during Fill, 182.3 ml of Plasma/Anticoagulant during Process (257.3 ml–75 ml for Surge bias) and some additional saline amounting to 19.2 ml during Surge. The output buffer delivers a "trickle" of saline for Fill and during the first 1.25 min. of Process, 167.1 ml of plasma/A.C. during the last approximately 3.04 minutes of Process and 34.4 ml during Surge. The net gain in fluid for the output buffer 62 at the conclusion of the First Pass is Zero.

For a product (platelet) volume of 35 ml, there would remain 40 ml of anticoagulant plasma left in the plasma bag, i.e., A.C. diluted plasma.

SECOND AND INTERMEDIATE PASSES

The remaining cycles, except the Last, consist of an Empty, Fill, Process and Surge sequence; the last is a modified Empty only cycle. It must be remembered that these state designations refer to bowl, item 10. During normal operation, pumps P1, P3 and P4 do not alter their speed/direction from the time when plasma is available during the first cycle through to the start of the last cycle.

Empty

At the beginning of the Empty cycle, transfer pump P2 is stopped, and Clamps C1, C3, C4, C7 and C8 are CLOSED while C2 and C6 are OPENED. The transfer pump P2 is then run in order to remove the blood remaining in bowl 10, removing fluid from port 14 and transferring it to the output buffer 60. To minimize process time the flow rate, controlled by P2, should be made as high as possible without causing significant cell damage.

A rate of 150 ml/min. is used in continuing the illustrative example. At this rate, a bowl fluid withdrawal time of about 1.67 minutes results (250 ml/150 ml per min.). The input buffer 24 would therefore contain about 137.5 ml at the time when the bowl has just been emptied:

$$37.5\ ml + (60\ ml\ per\ min. \times 1.67\ min.) = 137.5\ ml.$$

The output buffer 62 on the other hand would contain 158.3 ml.

$$250\ ml - (55\ ml\ per\ min. \times 1.5\ min.) = 158.3\ ml.$$

Fill

To fill the bowl 10, P2 is stopped, Clamps C1, C3 and C8 are CLOSED and Clamp C2 and C7 are OPENED. Next, weight sensor W1 is sampled to determine the volume of blood in input buffer 24. This volume, Vi, is used to determine the desired input flow rate for the bowl as follows:

$$Q2 = Q1[1 + (Vi/Bowl\ Vol. - Vi)] \qquad EQ.\ 1$$

Where Bowl Vol.=Bowl Volume (250 ml.)

For the example—

Vi=137.5 ml, Q1=60 ml/min. and Bowl Vol.=Bowl Volume=250 ml.

Therefore Q2=133.3 ml/min.

The time, Tf, required to fill the bowl (and empty the input buffer 24) is given by:

$$Tf = [Bowl\ Vol. - Vi]/Q1 \qquad EQ.\ 2$$

Therefore Tf=1.875 minutes.

Transfer pump P2 is then started and burned in a direction such that the fluid in the input buffer 24 is withdrawn and transferred through C7 and into bowl port 14 at a rate of about 133.33 ml/min.

At the end of the Fill time, the input buffer 24 fluid volume is just at its initial prime bias level of 10 to 20 ml. The output buffer 60 will have been depleted by pump P3, which during normal operation, continuously returns fluid to the donor from buffer 62, to a volume of 158.3−(55 ml per minute×1.875 minutes) which equals 55.2 ml.

Process

Once the bowl has filled, as confirmed by sensor S2, pump P2 is slowed to a rate Q2=Q1 in order to keep input buffer 24 in fluid equilibrium.

Now A.C. diluted plasma flows from the bowl output port 16 fluid and enters the plasma bag 28 at the rate Q1.

This will continue for about 0.583 minutes in order to replenish the 35 ml lost in the first pass described above. The weigher W2 is used to verify the proper transfer. At this point there remains around 23.1 ml in the output buffer 60.

$$55.2\ ml - (55\ ml\ per\ min. \times 0.583\ min.) = 23.1\ ml$$

With this transfer complete, clamp C8 is OPENED and C2 CLOSED. This is the condition until the optional Surge protocol begins—some 3.7 minutes later for the rates assumed for the example.

$$4.287\ min. - 0.583\ min. = 3.705\ min.$$

When the Process phase has concluded and the Surge beings, the input buffer 24 contains its minimum bias volume and the output buffer contains approximately 41.6 ml.

$$23.1\ ml + (60 - 55) ml\ per\ min. \times 3.705\ min. = 41.62\ min.$$

Surge

A Surge cycle is executed next as previously described above.

At the conclusion of Surge the input buffer 24 contains the same volume of A.C. diluted blood that it had when the First Pass concluded. For the example this is 37.5 ml.

After the Second Pass the Output buffer 60 contains 7.3 ml above its normal bias value, instead of 0 ml as achieved during the First Pass. This usually results because the amount of A.C. added per cycle slightly exceeds the amount of product volume sequestered.

$$\text{Total Cycle Time} \quad Tct = Te + Tf + Tp + Ts \qquad EQ.\ 3$$

(for each pass, from pass 2 to the next to last pass)

In the example $Te$ = (EMPTY) 1.67 min.,
$Tf$ = (FILL) 1.875 min.,
$Tp$ = (PROCESS) 4.287 min. and
$Ts$ = (SURGE) 0.625 min.
Then $Tct$ = 8.45 min.

Vol. of *A.C.* per Cycle,
$A$ = 5 ml per min. × 8.45 min. = 42.27 ml

Vol. of *A.C.* per Cycle − Product Vol. per cycle = Delta ($A - P$)

Delta ($A - P$) = 42.27 ml − 35 ml = 7.27 ml.

For N Cycles of processing the fluid gain in the output buffer 62 is:

$$(N-1) \times \text{Delta}\ (A-P) \qquad EQ.\ 4$$

Note:

If for a given ratio the product volume exceeds the A.C. added, then Saline would be added (opening C5) during the surge cycle. This would be sensed and compensated by using Weigher 3.

LAST PASS

The Last Pass is executed when the amount of product desired has been achieved and is performed as follows:

An Empty Cycle is initiated as described in above with the exception that the pumps P1 and P4 are halted. Therefore no additional fluid is collected in the input buffer 24 and the contents of the bowl 10 is transferred to the output buffer 62.

After the transfer is complete transfer pump P2 is halted. Clamps C7 and C8 are OPENED, C1 and C2 CLOSED, and P2 is used to transfer the bias volume in the input buffer 24 to the output buffer 62. When this task has been completed, as indicated by weigher W1, C7 is CLOSED and C3 and C8 OPENED. Pump P2 next transfers the residual plasma from Plasma Bag 28 to the output buffer 62. Weight sensor W2 indicates completion.

During all the above transfers P3 continues to empty the output buffer 62.

This last Pass is finished when all fluid in the output buffer has been withdrawn as indicated by Weigher 3.

The time required for the Last Pass is equal to the time it takes to transfer the volume of fluid comprising the sum of the bowl volume, the total excess anticoagulant volume, the input buffer bias and the left over plasma in bag 28, at the rate of pump P3.

For the example,

Time Duration of Final Pass=[250+(7×7.27)+20+40) ml]÷55 ml/min.

Total Procedure Time for a 2 ARM/8 Pass Example:

$$9.08\ min.+(7\times 8.45\ min.)+6.56\ min.\ 74.80\ min.=6.56\ min.$$

"First Pass+7 Intermediates+Last Pass" For Comparison, a Single Arm "Serial" Procedure with a comparable Draw rate would take approximately 97.6 minutes for 8 Passes.

| | |
|---|---|
| 8.45 min. | Draw/Process Time per Pass |
| +0.625 min. | Surge Time per Pass |
| +3.10 min. | Return Time per Pass (150 ml/min. Return Rate) |
| 12.2 min. | Pass |

Procedure Time = 8 × 12.2 min. = 97.6 min.

The advantages of 2 Arm Continuous Flow process of the invention over a Single Arm Serial Protocol are as follows:

1. An improvement in ECV (Extracorporeal Volume). Typically better than a 125 ml advantage.
2. Constant or nearly constant ECV. Single Arm Procedure requires about a unit of donor blood to be transferred back and forth, while the Two Arm Protocol maintains a nearly constant +/− 20 ml ECV.
3. Faster Procedure. Typically faster by better than 25%.

Equivalents

Those skilled in the art will recognize, or be able to ascertain, using no more than routine experimentation, many equivalents to the specific embodiments of the invention described herein.

These and all other equivalents are intended to be encompassed by the following claims.

We claim:

1. Apparatus comprising:

a) a draw needle for drawing whole blood from a donor;

b) an input buffer in fluid communication with said draw needle via a first conduit;

c) a second conduit for fluidly coupling anticoagulant fluid to said first conduit for mixing with said drawn blood;

d) a separator for separating drawn blood into at least two fractional components, said separator having an input port and an output port;

e) a third conduit for fluidly coupling the input buffer to the input port;

f) a component container;

g) a fourth conduit for fluidly coupling the output port to said container;

h) an output buffer;

i) a fifth conduit in fluid communication with said output buffer and said fourth conduit;

j) a sixth conduit in fluid communication between said output buffer and said third conduit;

k) a return needle in fluid communication with one or more of said output buffer or said component container for transferring fluid therefrom to said donor; and l) a seventh conduit for fluidly coupling said output buffer to a source of physiological solution.

2. The apparatus of claim 1 wherein the input buffer, output buffer and component container comprise plastic bags.

3. The apparatus of claim 1 wherein the separator comprises a centrifuge bowl.

4. The apparatus of claim 3 wherein the centrifuge bowl is comprised of a stationary input/output section coupled by a rotary seal to a rotating bowl section.

5. The apparatus of claim 1 including a pump for transferring said separated components and wherein one of the fractional components is plasma and wherein plasma is transferred from the output port to the component container.

6. The apparatus of claim 1 including a pump for transferring said separated components and wherein one of the fractional components is platelets and wherein platelets are transferred from the output port to the component container.

7. The apparatus of claim 1 wherein the physiological solution is saline.

8. The apparatus of claim 1 further including pump means for transferring anticoagulated whole blood into the input buffer.

9. The apparatus of claim 8 wherein anticoagulated whole blood in the input buffer is transferred by said pump means out of the input buffer to said input port at the same rate it is being transferred in.

10. The apparatus of claim 9 wherein fluid is transferred by said pump means from the output buffer to the donor at the same rate whole blood is being drawn from said donor.

11. Apparatus comprising:

a) a draw needle for drawing whole blood from a donor;

b) an input buffer in fluid communication with said draw needle via a first conduit;

c) a second conduit for fluidly coupling anticoagulant fluid to said first conduit for mixing with said drawn blood;

d) a separator for separating drawn blood into at least two fractional components, said separator having an input port and an output port;

e) a third conduit for fluidly coupling the input buffer to the input port;

f) a component container;

g) a fourth conduit for fluidly coupling the output port to said container;

h) an output buffer;

i) a fifth conduit in fluid communication with said output buffer and said fourth conduit;

j) a sixth conduit in fluid communication between said output buffer and said third conduit;

k) a return needle in fluid communication with one or more of said output buffer or said component container for transferring fluid therefrom to said donor via a seventh conduit;

l) a seventh conduit for fluidly coupling said output buffer to a source of physiological solution;

m) draw pump means coupled to said first conduit for transferring drawn blood from said draw needle to said input buffer;

n) A.C. pump means coupled to said second conduit for transferring anticoagulant from an anticoagulant source to mix with said drawn blood;

o) transfer pump means coupled to said third conduit for transferring in a first direction fluid from said input buffer to said input port and in a second direction fluid from said component container to said input port or to said output buffer; and p) return pump means coupled to said seventh conduit for transferring fluid from one or more of said output buffer or said component container to said donor.

12. The apparatus of claim 11 wherein the input buffer, output buffer and component container comprise plastic bags.

13. The apparatus of claim 11 wherein the separator comprises a centrifuge bowl.

14. The apparatus of claim 13 wherein the centrifuge bowl is comprised of a stationary input/output section coupled by a rotary seal to a rotating bowl section.

15. The apparatus of claim 11 including a pump for transferring said separated components and wherein one of the fractional components is plasma and wherein plasma is transferred from the output port to the component container.

16. The apparatus of claim 11 including a pump for transferring said separated components and wherein one of the fractional components is platelets and wherein platelets are transferred from the output port to the component container.

17. The apparatus of claim 11 wherein the physiological solution is saline.

18. The apparatus of claim 11 further including pump means for transferring anticoagulated whole blood into the input buffer.

19. The apparatus of claim 18 wherein anticoagulated whole blood in the input buffer is transferred by said pump means out of the input buffer to said input port at the same rate it is being transferred in.

20. The apparatus of claim 19 wherein fluid is transferred by said pump means from the output buffer to the donor at the same rate whole blood is being drawn from said donor.

21. A method for separating whole blood collected from a donor via a draw needle into constituent components and returning some of the separated components via a return needle in a centrifugal separation system comprised of a centrifuge having a stator and a rotatable bowl with the stator having an input port fluidly coupled on one side to an input reservoir and on another side to the interior of the bowl and an output port fluidly coupled on one side to the interior of the bowl and on another side to an output reservoir and a component container; comprising the steps of:

a) priming the system by transferring a volume of physiological solution from a solution bag into the output reservoir and transferring a volume of anticoagulant from an anticoagulant bag into the input reservoir and pumping some of the solution in the output reservoir to the return needle by a return pump;

b) drawing blood from the donor via the draw needle and mixing the blood with anticoagulant and transferring the anticoagulant drawn blood into the input reservoir by a draw pump;

c) transferring the physiological fluid from the output reservoir by the return pump into the donor via the return phlebotomy needle; and d) transferring the anticoagulated whole blood from the input reservoir to the input port of the bowl by a transfer pump causing some blood component(s) to be separated in the bowl and to exit the bowl and enter a component container for harvesting while other separated component(s) are transferred to said output reservoir; and e) transferring fluid from the output reservoir to the donor via the return phlebotomy needle.

22. The method of claim 21 wherein the input reservoir, output reservoir and component container are formed of disposable plastic bags.

23. The method of claim 21 wherein the transferring is performed by pumps.

24. The method of claim 21 wherein the pumps are peristaltic type pumps.

25. The method of claim 21 including a pump for transferring said separated components and wherein one of the fractional components is plasma and wherein plasma is transferred from the output port to the component container.

26. The method of claim 21 including a pump for transferring said separated components and wherein one of the fractional components is platelets and wherein platelets are transferred from the output port to the component container.

27. The method of claim 21 wherein the physiological solution is saline.

28. The method of claim 21 further including pump means for transferring anticoagulated whole blood into the input reservoir.

29. The method of claim 21 wherein anticoagulated whole blood in the input reservoir is transferred out of the input reservoir to said input port at the same rate it is being transferred in.

30. The method of claim 21 wherein fluid is transferred from the output reservoir to the donor at the same rate whole blood is being drawn from said donor.

* * * * *